United States Patent [19]
Theodore

[11] Patent Number: 5,759,545
[45] Date of Patent: Jun. 2, 1998

[54] METHOD FOR THE TREATMENT OF HIV-I INFECTION

[76] Inventor: T. Ronald Theodore, P.O. Box 513, Forestdale, Mass. 02644

[21] Appl. No.: 806,742

[22] Filed: Feb. 27, 1997

Related U.S. Application Data

[60] Provisional application No. 60/012,351 Feb. 27, 1996.

[51] Int. Cl.⁶ .................................................. A01N 63/00
[52] U.S. Cl. ...................................... 424/160.1; 424/159.1
[58] Field of Search ........................... 424/141.1, 147.1, 424/148.1, 156.1, 159.1, 160.1, 172.1, 188.1, 208.1, 93.21, 537, 561, 809, 810; 514/2, 21, 934

[56] References Cited

PUBLICATIONS

Wolff et al. "Lymphadenopathy Associated Virus/Human T–cell Lymphotropic Virus III Antibodies in Homosexual Men with and without Sperm Antibodies", *Fertility And Sterility*, vol. 46, No. 1 (Jul. 1986), pp. 111–3, RC889.A532.

*Primary Examiner*—Jeffrey Stucker
*Attorney, Agent, or Firm*—Richard P. Crowley

[57] ABSTRACT

A method for the treatment of the AIDS virus in a mammal, which method comprises administering to the mammal having the AIDS virus a therapeutic, effective amount of a human antispermatozoal antibody, or monoclonal antibodies derived therefrom, used alone or in combination with plasma, serum or purified immunoglobulin, and combinations thereof.

7 Claims, No Drawings

METHOD FOR THE TREATMENT OF HIV-I INFECTION

REFERENCE TO PRIOR APPLICATIONS

This application claims the priority benefit of U.S. provisional patent application Ser. No. 60/012,351, filed Feb. 27, 1996.

BACKGROUND OF THE INVENTION

AIDS is the single most discussed, dangerous and unforgiving disease throughout the planet. It requires the attention of the world as the most serious emergent health problem today. It also poses a major economic threat. It is anticipated that tens of millions of people will succumb to this disease over the next few years. It is a disease that affects and kills children as much as it does adults. AIDS knows no social or economic boundaries.

It is desirable to provide a method for the treatment of AIDS, and other viral or infectious diseases, using specific antibodies.

SUMMARY OF THE INVENTION

The invention relates to a method of treating infectious diseases in mammals, particularly viral diseases, such as AIDS, employing antispermatozoal antibodies (ASA).

The ASA is typically administered by injection with a liquid composition (e.g., saline-buffered) containing ASA used in an effective concentration, either alone or in combination with additives or modifying amounts of plasma, serum, or purified immunoglobulin.

At present there is no current effective drug protocol for AIDS and there is an apparent failure for vaccine products to either prevent the transmission of the virus or retard its growth within infected cells or organisms.

A new method and system for the treatment of various infectious and immunologic diseases is described. The method and system involve the use of antibodies which singularly or multiply are directed towards the proteins that envelope cell membranes in the pathogen and/or host systems. These antibodies will block the envelope proteins or other proteins from effecting either direct or indirect action on the cell membrane wall or inhibit the protein effect intracellularly, extracellularly or intercellularly.

The initial use of this method and system is directed towards, but not limited to, the AIDS viruses. The envelope proteins of the HIV-I virus have been shown to enter and destroy certain T-cells without the virus being present. Virtually all patients with the HIV-I virus make antibodies to the virus, but these antibodies effect no protection.

It is shown that certain proteins secreted by sperm will allow entrance to the ova. The method and system described utilizes natural or synthetic, monoclonal antibodies to sperm which inhibit sperm entry into the ova by effect on sperm envelope proteins and will effect similar action on the envelope proteins of the AIDS or other viruses. These proteins, which are normally either destroyed or consumed, are toxic to the system in certain pathological states. It is shown that by inhibiting the entrance of these toxic proteins by antibodies, the virus cannot enter the cells where they can replicate and produce more toxic protein and continue the cycle.

It is shown that toxic proteins may effect similar situations in other infectious, immunologic, hematologic and oncologic states. A similar situation may be effected by antibodies produced against normal (host) cells and abnormal (pathogenic) cells that results in the inability for envelope and other proteins to be produced, and thus effect a toxic response.

The method is an innovative approach to controlled transmission and progression of HIV-I virus infection which leads to a means of easing the progression of AIDS.

The invention comprises a method to treat diseases by using human antispermatozoal antibodies (ASA). There are three types of ASA that are natural. Two are antibodies to the sperm head and one is an antibody to the sperm tail. The tail antibodies affect mobility of the sperm. The functions of the head antibodies are not totally understood, but can affect the ability of the sperm to enter an ovum.

The concentration of the ASA antibody that is effective covers a broad range depending on the effect to be had on a given disease state.

In one embodiment human antispermatozoal antibodies in an immunoglobulin fraction having a size of 0.1 to 500 µg are injected in concentrations of about 1 to 10,000 µg/ml in varying amounts to mammals, with varying time frequency; e.g., 1 to 30 days.

The presence of the ASA can alter and/or effect and/or affect different disease states. Such states may be due to viral infections, such as HIV-I, and/or immunological states, such as rheumatoid arthritis, and/or cancer.

Viruses have protein coats. Specifically, the protein of the HIV-I is molecularly similar to the protein coat of the spermatozoa. Thus, the reason that the HIV-I is not normally found in spermatozoa is that the virus, in essence, sees itself. It is shown that antispermatozoal antibodies (ASA) have cross-reactivity with HIV-I antigen. Specifically, when HIV-I antigen is combined with ASA antigen activity measurements are decreased. Further, in the presence of ASA, HIV total load as measured in vivo is reduced.

Many viruses with a molecular protein coat similar to the spermatozoal coat will be bound to some degree, more or less, by the ASA. In addition, binding of ASA to molecularly similar coats (as sperm) affects the ability of the virus to replicate. Once the virus is unable to replicate, it will die.

Certain cancer cells have protein coats molecularly similar to ASA. This is shown in the ability of certain cancer cells to replicate in the presence of ASA, and which cells are reduced and/or stopped by the attachment of the ASA to the cell membrane at antibody binding sites. The effect of bindings is to alter the ability of the cell to replicate.

Certain immunological states are caused by certain protein substances that are developed and/or produced and/or result from certain biological conditions, disease states, environmental effects and toxins. These protein and/or protein-like substances will bind to ASA. This binding reduces and/or slows and/or halts and/or reverses the viral disease process.

It has been discovered that the ability of ASA to bind to molecularly similar proteins, protein coats and protein molecules has measurable changes in measurements on protein levels and/or activity and/or production of these proteins. The changes in measurements result in adequate tests to prognosticate disease progression and/or regression and/or to determine levels of disease activity and/or assessment of treatment modalities. At this time, there is no effective medical means for preventing HIV-I infection. Current approaches to control this epidemic are either: (1) preventing transmission by avoidance behavior (sexual abstinence or physical barriers to transmission during contact; e.g., using condoms); or (2) inhibiting replication of the virus in cells of the host (acyclovir or AZT).

After infection, there is no effective medical treatment. This means once acquired, the HIV-I leads to a progressive immunosuppression that is ultimately fatal.

AIDS is presumed to be transmitted by the attachment of the HIV-I virus to a specific cell surface site which accepts the entry and incorporation of the virus. Interference with the mechanics of the attachment may affect transmission of the virus between cells in the same individual or between different individuals.

This is analogous to the neutralization effect of antiviral antibodies in other viral infections. One rationale for treatment and prevention of AIDS by this invention is to prevent the transmission of the HIV-I to susceptible cells by the inhibition of viral attachment. The method of treatment is the evidence that a part of a normal human cell functions as a receptor for the binding of the infectious HIV-I.

The method uses specific attachment of the virus to inhibit by naturally occurring antibodies, thus modifying the infection of the lymphoid cells that result in immune deficiency, the ultimate hallmark of the disorder. Inducting antibodies against certain normal cell surface components may result in antibodies that cross-react with host cell receptors for the HIV-I. The method is tested by demonstrating the antibody cross-reactively using specific laboratory approaches.

An effective method for modification of progression of HIV-I and HIV-II consists of seven steps:

1. Measurement and documentation of valid sera containing the specific antibody to "Prime" samples.
2. Measurement of anti-HIV-I and anti-HIV-II antibodies through ELISA testing. Northern Blot confirmation can be obtained on all positive samples. Further measurement of anti-HIV functional antibodies is done by detecting the ability of the sera to impair the penetration of HIV into cell monolayers.
3. Special studies to absorb valid sera with sources of "Prime" samples. "Prime" samples are obtained from a genetically disparate pool that is available.
4. Absorption of valid sera with HIV-I and HIV-II.
5. Repeat assessment of antibody reactivities utilizing the absorbed serum.
6. Where sera tested above are positive, we titer the antibody activities before and after absorption. This allows correlation of the antibody activities and demonstrates that the same antibodies are present in both studies. In addition, testing can show whether the cross-reactivity is competitive, non-competitive or uncompetitive by appropriate dilutional studies. This is an appropriate way of measuring whether the antibodies against the "Prime" source and antibodies against HIV-I are actually directed against the same target.
7. Finally, measurement of HIV-I positive sera against "Prime" samples to see if the disease per se leads to the production of anti-"Prime" antibodies. It is possible that the cross-reactions between the "Prime" and HIV-I samples are not symmetric; i.e., HIV-I-infected individuals may or may not make anti-"Prime" antibody. Similarly, individuals sensitized against "Prime" samples may or may not make anti-HIV antibody. It is important to look at HIV-I sera as additional confirmation of the method.

DESCRIPTION OF THE EMBODIMENTS

EXAMPLE 1

Samples of human antispermatozoal antibodies were obtained consisting of human serum from antibody-positive females. The serum contained all forms of antispermatozoal antibodies as naturally occurring. Samples of HIV-I antigens without any virus or viral particles were obtained. The samples were combined by standard mixing techniques and studied under standard in vitro conditions. Immunofluorescent techniques evidenced moderate cross-reactivity between the antibodies and the antigens.

EXAMPLE 2

An ASA in a immunoglobulin fraction of 1.0 to 200 µg is prepared at concentrations of 100 to 5000 µg/ml and is injected into three mammals (humans) who are tested positive for HIV-I and is confirmed by Western Blot analysis. Total viral load is measured by PCR (Polymerase Chain Reaction). In each case, total viral load decreased by 25 percent or more over 90 to 180 days.

What is claimed is:

1. A method for the treating of a mammal having a HIV-1 infection, which method consists essentially of:

administering to the mammal an effective therapeutic amount of antispermatozoal antibodies (ASA) to reduce the HIV-1 load of the mammal the antibodies specific for the head of the sperm, and wherein the HIV-1 infection is derived from a protein which has the same or similar molecule coat as the ASA.

2. The method of claim 1 which includes administering the ASA by injecting a liquid purified immunoglobulin fraction of ASA into the mammal.

3. The method of claim 2 wherein the immunoglobulin fraction has a size of 0.1 to 500 µg.

4. The method of claim 1 which includes administering an amount of from about 1.0 to 10,000 µg per ml of the ASA.

5. The method of claim 4 which includes administering the amount over a period of about 1 to 30 days.

6. The method of claim 1 wherein the total viral load of the mammal after administering decreases by 25 percent or more.

7. A method for the treating of a mammal having an HIV-1 infection, which method consists essentially of:

injecting into the HIV-1 infected mammal an effective therapeutic amount of from 0.1 to 10,000 µg per ml over a selected time period of a liquid purified immunoglobulin fraction containing antispematozoal antibodies (ASA) derived from the head of human sperm to reduce the viral load of the mammal.

* * * * *